United States Patent
Manzke et al.

(10) Patent No.: US 10,448,837 B2
(45) Date of Patent: Oct. 22, 2019

(54) MAPPING SYSTEM AND METHOD FOR MEDICAL PROCEDURES

(75) Inventors: Robert Manzke, Eindhoven (NL); Raymond Emmanuel Chan, Eindhoven (NL); Adrien Desjardins, Eindhoven (NL); Gert Wim 'T Hooft, Eindhoven (NL); Szabolcs Deladi, Eindhoven (NL)

(73) Assignee: KNONKLIJKE PHILIPS N.V., Eindhoven (NL)

( * ) Notice: Subject to any disclaimer, the term of this patent is extended or adjusted under 35 U.S.C. 154(b) by 596 days.

(21) Appl. No.: 13/817,263

(22) PCT Filed: Aug. 17, 2011

(86) PCT No.: PCT/IB2011/053637
§ 371 (c)(1),
(2), (4) Date: Feb. 15, 2013

(87) PCT Pub. No.: WO2012/025856
PCT Pub. Date: Mar. 1, 2012

(65) Prior Publication Data
US 2013/0150732 A1    Jun. 13, 2013

Related U.S. Application Data

(60) Provisional application No. 61/375,947, filed on Aug. 23, 2010.

(51) Int. Cl.
*A61B 5/00* (2006.01)
*A61B 1/00* (2006.01)
(Continued)

(52) U.S. Cl.
CPC ........ *A61B 5/0084* (2013.01); *A61B 1/00009* (2013.01); *A61B 1/0017* (2013.01);
(Continued)

(58) Field of Classification Search
CPC ......... A61B 5/06; A61B 5/0084; A61B 5/055; A61B 5/6855; A61B 5/6856;
(Continued)

(56) References Cited

U.S. PATENT DOCUMENTS 6,004,269 A * 12/1999 Crowley et al. .............. 600/439
7,720,322 B2 5/2010 Prisco
(Continued)

FOREIGN PATENT DOCUMENTS

WO   WO200113060    2/2001
WO   WO2006092707   9/2006
(Continued)

OTHER PUBLICATIONS

F. Banovac et al., "Radiofrequency Ablation of Lung Tumors in Swine Assisted by a Navigation Device with Preprocedural Volumetric Planning", (Abstract) Journal of Vascular and Interventional Radiology, vol. 21, Issue 1.
(Continued)

*Primary Examiner* — Amanda Lauritzen Moher
*Assistant Examiner* — Katherine M McDonald

(57) ABSTRACT

A system and method for mapping interluminal structures includes an elongated flexible instrument (102). An optical shape sensing device (152, 154) is disposed within the flexible instrument and is configured to determine a shape of the flexible instrument relative to a reference. The shape sensing device is configured to collect information based on its configuration to map an interluminal structure during a procedure. An imaging enabled ablation device (117) is mounted at or near a distal end portion of the flexible instrument.

7 Claims, 5 Drawing Sheets

(51) Int. Cl.
| | |
|---|---|
| A61B 1/018 | (2006.01) |
| A61B 17/00 | (2006.01) |
| A61B 18/14 | (2006.01) |
| A61B 1/04 | (2006.01) |
| A61B 1/05 | (2006.01) |
| A61B 1/06 | (2006.01) |
| A61B 1/07 | (2006.01) |
| A61B 5/055 | (2006.01) |
| A61B 6/03 | (2006.01) |
| A61B 8/08 | (2006.01) |
| A61B 8/12 | (2006.01) |
| A61M 25/00 | (2006.01) |
| A61B 34/20 | (2016.01) |
| A61B 18/00 | (2006.01) |
| A61B 8/00 | (2006.01) |
| A61B 90/00 | (2016.01) |
| A61B 90/30 | (2016.01) |

(52) U.S. Cl.
CPC ...... *A61B 1/00045* (2013.01); *A61B 1/00087* (2013.01); *A61B 1/00094* (2013.01); *A61B 1/018* (2013.01); *A61B 1/042* (2013.01); *A61B 1/051* (2013.01); *A61B 1/0676* (2013.01); *A61B 1/07* (2013.01); *A61B 5/0037* (2013.01); *A61B 5/0044* (2013.01); *A61B 5/055* (2013.01); *A61B 5/4836* (2013.01); *A61B 5/6856* (2013.01); *A61B 5/6857* (2013.01); *A61B 5/72* (2013.01); *A61B 5/742* (2013.01); *A61B 6/032* (2013.01); *A61B 8/0883* (2013.01); *A61B 8/12* (2013.01); *A61B 8/5238* (2013.01); *A61B 17/00234* (2013.01); *A61B 18/1492* (2013.01); *A61B 34/20* (2016.02); *A61M 25/0082* (2013.01); *A61B 8/461* (2013.01); *A61B 2017/003* (2013.01); *A61B 2017/00053* (2013.01); *A61B 2017/00247* (2013.01); *A61B 2018/00392* (2013.01); *A61B 2034/2061* (2016.02); *A61B 2090/306* (2016.02); *A61B 2090/374* (2016.02); *A61B 2090/376* (2016.02); *A61B 2090/3762* (2016.02)

(58) Field of Classification Search
CPC ... A61B 5/6857; A61B 5/6846; A61B 5/6847; A61B 5/6852; A61B 5/0044; A61B 1/042; A61B 1/0676
USPC ........................................................ 600/478
See application file for complete search history.

(56) References Cited

U.S. PATENT DOCUMENTS

| | | | |
|---|---|---|---|
| 7,772,541 B2 * | 8/2010 | Froggatt | G01M 11/083 250/226 |
| 8,050,739 B2 | 11/2011 | Eck et al. | |
| 8,182,433 B2 | 5/2012 | Leo et al. | |
| 8,437,518 B2 | 5/2013 | Chan et al. | |
| 2006/0013523 A1 | 1/2006 | Childlers et al. | |
| 2009/0137952 A1 * | 5/2009 | Ramamurthy | A61B 5/06 604/95.01 |
| 2010/0030063 A1 * | 2/2010 | Lee et al. | 600/424 |
| 2010/0056904 A1 | 3/2010 | Saunders et al. | |
| 2010/0099951 A1 * | 4/2010 | Laby | A61B 1/0052 600/144 |
| 2012/0105480 A1 * | 5/2012 | Barley | A61B 19/52 345/641 |

FOREIGN PATENT DOCUMENTS

| | | |
|---|---|---|
| WO | WO2008131303 | 10/2008 |
| WO | WO2009138957 | 11/2009 |
| WO | WO2010064154 | 6/2010 |

OTHER PUBLICATIONS

Z. Lunwei et al., "FBG Sensor Devices for Spatial Shape Detection of Intelligent Colonoscope", Proceedings of the 2004 IEEE International Conference on Robotics & Automation, New Orleans LA, Apr. 2004, pp. 835-840.

* cited by examiner

MAPPING SYSTEM AND METHOD FOR MEDICAL PROCEDURES

This disclosure relates to medical imaging, and more particularly to systems and methods for mapping internal volumes using a combination of shape sensing and images during medical procedures.

Complex ablation procedures such as atrial fibrillation (AF) ablation are typically performed using electroanatomic mapping (EAM) systems in combination with interventional X-ray imaging. Different enhancements have been attempted for imaging capabilities for an ablation device to obtain better feedback on lesion formation. Ultrasound, photoacoustics, magnetic resonance imaging (MRI) or other techniques are being investigated for this purpose.

For example, Voyage Medical, Inc. has developed an ablation catheter with optical endoscopic imaging capabilities. During ablation, the superficial tissue protein denaturation during ablation can be appreciated visually. However, the technology currently lacks the ability to interrogate tissue depth for assessment of lesion transmurality.

In accordance with the present principles, systems and methods are provided that permit for combined electroanatomic mapping (EAM) and lesion formation mapping by adding a shape sensing aspect to a catheter or scope inserted within a body. In one embodiment, an optical shape sensing system is employed to track lesion imaging enabled ablation devices. The present systems also permit for rapid acquisition of three-dimensional (3D) volumetric sweeps of a catheter or a scope's elongated distal segment. This provides a painted electronic mapping of a 3D volumetric space, and provides volumetric point clouds which can facilitate registration and segmentation of intra-/pre-procedurally acquired datasets.

The present principles can provide benefits such as, e.g., better feedback for a physician on location and quality of ablation lesions within an anatomy. A more detailed anatomic map for ablation procedures is realized including the location and quality of lesions. Faster and more accurate sampling of dense point clouds for anatomy delineation is achieved. Simpler registration is provided with pre-operative image data based on the dense point clouds provided from the shape sensing.

A system and method for mapping interluminal structures includes an elongated flexible instrument. An optical shape sensing device is disposed within the flexible instrument and is configured to determine a shape of the flexible instrument relative to a reference. The shape sensing device is configured to collect information based on its configuration to map an interluminal structure during a procedure. An imaging enabled ablation device is mounted at or near a distal end portion of the flexible instrument.

Another system for mapping interluminal structures includes an elongated flexible instrument and an optical shape sensing device disposed within the flexible instrument and configured to determine a shape of the flexible instrument relative to a reference. The shape sensing device is configured to collect information based on its configuration during a procedure. An imaging enabled ablation device is mounted at or near a distal end portion of the flexible instrument. A shape sensing module is configured to receive the information collected by the shape sensing device and generate a map of an interluminal structure.

A method for interluminal mapping includes guiding an elongated flexible instrument having an optical shape sensing device to a region of interest; determining a shape of the flexible instrument relative to a reference; collecting information about surfaces in the region of interest by sweeping the shape sensing device along a surface to generate an electroanatomic map of the region of interest; and performing a procedure using at least the electroanatomic map.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
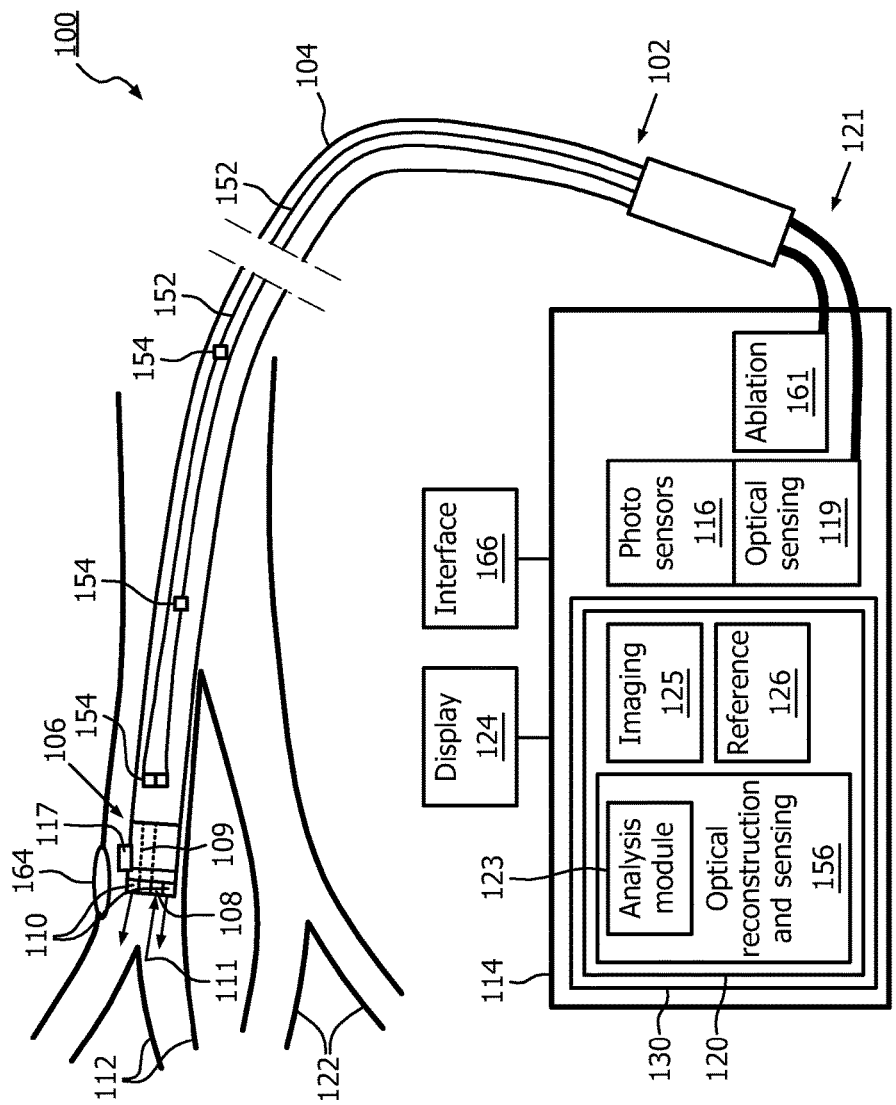
FIG. 1 is a diagram showing a system for interluminal mapping using an optical shape sensing device in accordance with the present principles.

The present disclosure describes systems and methods for an imaging enabled ablation device in combination with an optical shape sensing fiber tracking system, which forms an advanced ablation system capable of generating electroanatomic maps in combination with lesion quality information. The present embodiments make use of shape reconstruction capabilities of optical sensing shape-based volumetric definition for live processing of pre and intra-operative 3D imaging data.

Complex ablation procedures such as atrial fibrillation (AF) ablation are often performed using electroanatomic mapping (EAM) systems in combination with interventional X-ray imaging. In such systems, the ablation device would benefit from better imaging capabilities to obtain better feedback on lesion formation. In accordance with the present principles, a system combines EAM and lesion formation mapping by adding optical shape sensing based on, e.g., Fiber Bragg Gratings (FBGs), Rayleigh scattering or other optical effects or parameters, to imaging-enabled ablation devices. Incorporation of shape sensing over a distributed catheter length also allows for novel "painting" of catheter tip loci in 3D, providing rapid acquisitions of volumetric point clouds which can be used to facilitate registration and segmentation processes.

It should be understood that the present invention will be described in terms of optical shape sensing using Fiber Bragg Gratings, Rayleigh scattering or the like; however, the teachings of the present invention are much broader and are applicable to any components that can be mounted on, positioned on or otherwise placed on a catheter or endoscope to track a shape or position of that device during a procedure. It also should be understood that the present invention will be described in terms of medical instruments, such as ablation devices; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc.

The elements depicted in the FIGS. may be implemented in various combinations of hardware and software and provide functions which may be combined in a single element or multiple elements. The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

Referring now to the drawings in which like numerals represent the same or similar elements and initially to FIG. 1, an optical scope or catheter system 100 is illustratively shown. System 100 includes a scope or device 102, such as a catheter, a fiber optic scope, or a scope with a camera 108 employed in viewing or interacting with internal cavities and in particular blood or airway passages in a living organism. Scope or device 102 includes a flexible cable 104 that may include an optical fiber for conveying visual images. The device 102 can include a working channel 109 along its length for aspiration or insertion of tools. A tip 106 on a distal end portion of the cable 104 includes camera 108 and at least one light source 110. Depending on the system, the light source 110 may be affixed on the end portion of the device 102 or light may be transmitted from a proximal end of the cable or other flexible instrument 104 through a fiber optic link. Tip 106 may also include other tools or attachments depending on the application and procedure. The fiber optic scope or device 102 may include a charge coupled device (CCD) camera at the proximal end of the cable 104, while the video scope may include a CCD camera set close to or on the tip 106.

Light reflected 111 from walls of internal tissues 122 is detected and propagated down the cable 104 as optical (or electrical) signals. The signals are interpreted preferably using a processor or processing device 114, such as a computer or other platform configured with a photosensing device 116 in the case of a distally disposed camera. Photosensing device 116 may be mounted on a printed circuit board, be included in a camera device (e.g., a CCD camera) or be integrated in an integrated circuit chip. Many configurations and implementations may be employed to decipher and interpret the optical signals. If the camera is included in the tip 106, the signals are converted to electrical signals and interpreted by the processing device without photosensing device 116. Other configurations may include ultrasonic imaging or the like.

An ablation electrode(s) 117 may be provided on the distal end portion of the device 102. The electrodes 117 may take on any number of configurations and may be retractable. An ablation controller 161 may be employed to energize and otherwise control the ablation process (e.g., using RF energy or electrical current).

Device 102 preferably includes a flexible elongated instrument that permits a plurality of optical fibers 152 configured with sensors 154, such as FBGs, intrinsic Rayleigh scattering or any other optical shape sensing setup, to extend longitudinally along the length of device 102. Simultaneous measurements of strain due to the flexing of the device 102 can be measured and segmental motion of the device 102 can be tracked. Simultaneous measurements may be made in a distributed fashion to determine a configuration and shape of the device 102 over time. The device 102 will have its deformation tracked to measure biological tissue during a procedure, e.g., monitoring tissue-induced strains in the fiber optic tracking system in a looped catheter to estimate electromechanical synchrony or to estimate intervention impact on cardiac contractility. In this way, deflection experienced by device 102 may be correlated to deformations of tissue surrounding the device 102 to create a volumetric map.

The device 102 includes strain sensors 154 which are disposed over an elongated section of the device 102. The shape sensing system will have many (e.g., thousands) of strain sensors 154 comprised of FBGs or intrinsic Rayleigh scatter patterns of finite segments of the optical fiber 152. Other numbers of fibers and sensors may also be employed.

Optical shape sensing may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector. The principle behind the operation of a fiber Bragg grating is Fresnel reflection at each of the interfaces where the refractive index is changing. For some wavelengths the reflected light of the various periods is in phase with one another so that constructive interference exists for reflection and consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One of the main advantages of the technique is that various sensor elements can be distributed over the length of a fiber. Incorporating three or more cores with various sensors (gauges) along the length of a fiber that is embedded in a structure allows for the three dimensional form of such a structure to be precisely determined. Along the length of the fiber, at various positions, a multitude of FBG sensors are located (e.g., three or more fiber sensing cores). From the strain measurement of each FBG the curvature of the structure can be inferred at that position. From the multitude of measured positions, the total three dimensional form is determined. As an alternative to fiber optic Bragg gratings, the inherent backscatter in optical fibers, can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in 3 or more cores running within a single length of multicore fiber, the 3D shape and dynamics of the surface of interest would be trackable.

The fibers 152 are introduced into the body of the instrument 102 with a dense series of fiber Bragg gratings 154 or optical fiber intrinsic Rayleigh scatter pattern segments spatially distributed along its length and/or clustered in functional regions of the instrument. The sensors 154 may form an array to collect data over a region. Each fiber 152 may include one or more sensors 154. The optical shape sensing device (e.g., fibers 152 and gratings 154) may include areas of higher sensitivity by including an area with a higher number of optical fibers having Fiber Bragg Gratings (FBGs) or Rayleigh scatter segments.

The sensors 154 may include uncoated FBGs or Rayleigh scatter segments for shape sensing. Other optical or electronic sensors may also be employed. Device 102 may include an optical module, FBG, Rayleigh scatter or the like module 119 for sense fiber illumination and receiving fiber signals. The source of module 119 may be at a proximate end portion of the device and carry light to and from the fiber 152. The module 119 receives and processes the optical signals for use with other aspects of the system 100 including shape sensing.

Module 119 may be employed for readout of multiplexed signals returning from optical shape sensing fibers 154 in all fibers 152. Computing device 114 may include a real-time reconstruction program 156 for sensing fiber shape and volumetric mapping. The computing device or console 114 is configured for real-time interaction and visual display of instrument location and spatially distributed measurements (e.g., strain-derived biophysical measurements, endoscope-based video or other imaging data, catheter-based video or other imaging data).

The device 102 may optionally include other features such as conventional sensors or may include a stabilizing/fixation mechanism for holding a point on the sensing fiber fixed against a reference location of interest (e.g. a balloon with or without perforations to allow for flow past the fixation point). Other functions may also be provided.

The device 102 may be employed in conjunction with imaging data acquired either pre-procedurally, intra-procedurally, or simultaneously with optical interrogation. Imaging and optical data recordings can be used in combination to improve the estimates of biophysical parameters, mapping information, instrument characteristics and tissue properties to make decisions about interventional procedure guidance and monitor therapy progress.

System 100 includes a connection 121 to/from device 102 for optical interrogation output to provide a read-out of fiber shape, provide power to other features (e.g., ablation, etc.) and send and receive any other signals. The instrument data acquired may be carried on connection 121, e.g., real-time video (e.g., from a video endoscope), real-time ultrasound (e.g., from an intracardiac echo, ICE catheter), light for FBGs, Rayleigh scatter patterns, etc. Power to instrument therapy mechanisms (e.g. electrode 117) are provided through connection 121 such as RF power for an RF ablation catheter, etc. The connection 121 to the shape sensing-enabled instrument 102 also provides information to/from a medical imaging system 125. Feedback and control signals may be exchanged through connection 121. For example, instrument navigation may be employed as feedback based on shape sensing interrogation to assist in guiding the instrument 102. In addition, feedback or control signals may be employed for volumetric mapping based on optical shape sensing interrogation.

System 100 may include multiple processing or computing devices 114 for generating control signals, performing computations, generating video images, interpreting feedback, etc. For example, processing of distributed optical shape measurements permits segment mapping of internal regions of a patient. In particularly useful embodiments, segments of the device 102 can monitor a swept path of sensors mapped to provide a volumetric map of the internal anatomy of a patient. Surfaces engaged during a procedure, e.g., tissue-induced fiber optic strains, can be provided as dimensional feedback of the internal passageways and cavities inside a patient. This information provides a map, designates a location of a lesion so that the lesion can be located later and provides a reference to estimate changes in the lesion over time or as a result of treatment.

The user may store data in memory 120. Memory 120 may include programs (e.g., program 156). The program 156 may be adapted to take measurements and control sensors (e.g., FBGs, Rayleigh scatter segments). A display 124 may be provided for visualizing procedures and/or for interfacing with the console 114 and device 102 during a procedure. The user may employ a user interface 166 to interact with the console 114 and/or the device 102. The interface 166 may include a keyboard, a mouse, a touch screen system, etc.

Processing device or console 114 may be or include a computer device, processor or controller 130 configured to implement program 156 or other programs. Program 156 includes instructions for interpreting and executing functions in accordance with the present principles. Program 156 includes a shape sensing feature that determines and interprets sensor positions for, e.g., the Fiber Bragg Gratings (FBGs) 154 or intrinsic Rayleigh scatter segments of the optical fiber or the like.

Features of the program 156 may include an analysis program 123 to identify internal structures and features based upon feedback from the optical shape sensors 154. Anatomical references 112 may also be recognized and stored are references 126 in memory 120. These references 126 may be compared to a 3D topology map taken earlier (e.g., pre-op). Topology mapping may be compared to an atlas of a patient's anatomy or a general anatomical model. The qualitative shape of a region of interest can be obtained using images from the camera 108 and shape sensing of the device 102 using optical interrogation provided by program 156.

In a particularly useful embodiment, device 102 includes an ablation lesion imaging enabled catheter/device in combination with optical shape sensing tracking. Using the features of device 102 and console 114 an advanced mapping system for complex cardiac ablation procedures is realized. The optical shape sensing fiber 152 is integrated into the device 102 for tracking the catheter over an extended length from the distal tip. The tracked device 102 can be used to generate electroanatomic maps with ablation lesion depth information visualized using camera 108 on the anatomic surface.

In one embodiment, a retrofitted configuration for optical shape sensing integration into the ablation monitoring catheter may include inserting a shape sensing enabled optical fiber into an irrigation channel or a working channel 109 of device 102, while taking appropriate measures at the proximal end of the catheter to separate the fluidics from optical fiber connection. Conventional EAM systems usually require a six degree of freedom (DOF) coil at the tip of the ablation catheter which is electromagnetically tracked. This adds complexity to the device tip and requires tedious and time consuming individual point sampling within the anatomy. Other EAM systems employ a multitude of electrodes that are tracked inside the heart using impedance measurements. While this is faster then using a coil, less accurate point sampling within the anatomy is experienced.

In accordance with the present principles, using optical shape sensing tracking permits for highly accurate shape sensing along a significant length of a catheter. This shape sensing can be used for rapid and highly accurate dense point cloud sampling within the anatomy of interest, allowing for rapid anatomical map definition.

In accordance with the present principles, an integrated optical shape sensing device with an ablation/mapping catheter permits rapid acquisition of 3D volumetric sweeps of the catheter distal segment or other segments. This effectively permits "painting" or surface mapping of detailed, ultra-dense volumetric point clouds which can facilitate registration and segmentation of intra-/pre-procedurally acquired datasets.

Figure 2:
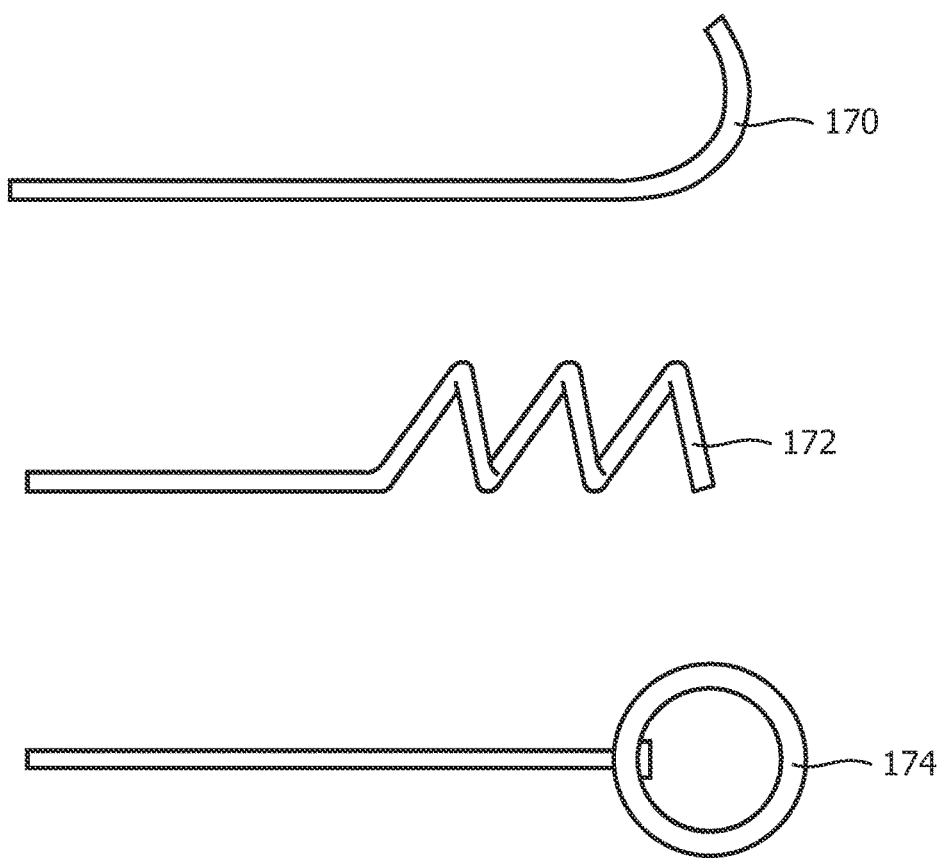
FIG. 2 is a diagram showing different configurations of a catheter tip which may be employed to sweep a region of interest to be mapped in accordance with the present principles.

Referring to FIG. 2, different catheter shapes or configurations can permit faster interrogation of a chamber anatomy. These shapes may include, e.g., loops, spirals, rings, etc. of the catheter itself, which could be tracked more accurately and with highly dense spatial sampling. In the examples depicted in FIG. 2, loops 170, spirals 172, and rings 174 are illustratively depicted. The real-time behavior of a distal tip shape can be steered by the physician to allow for new interaction modes with the imaging system (e.g., allowing for catheter shape based system input by the physician).

Single forward-looking ablation monitoring catheters (device 102 in FIG. 1) would benefit from optical shape sensing integration, since the shape of the distal end of the catheter could be used to optimally direct the catheter tip towards the tissue (e.g., lesion 164), and obtain contact angles of, e.g., 90±20 degrees.

Registration of intra- or pre-operative anatomic meshes (e.g. from rotational X-ray or CT) with intra-operatively acquired anatomic maps (point clouds) can be performed using, for example, an iterative closest point (ICP) algorithm. The highly accurate information from optical shape sensing can be used to improve the registration by particularly interrogating dominantly shape-defining anatomic landmarks (e.g., those areas with high surface curvature, for example, an anatomical ridge such as at pulmonary veins or left atrial boundaries).

Figure 3:
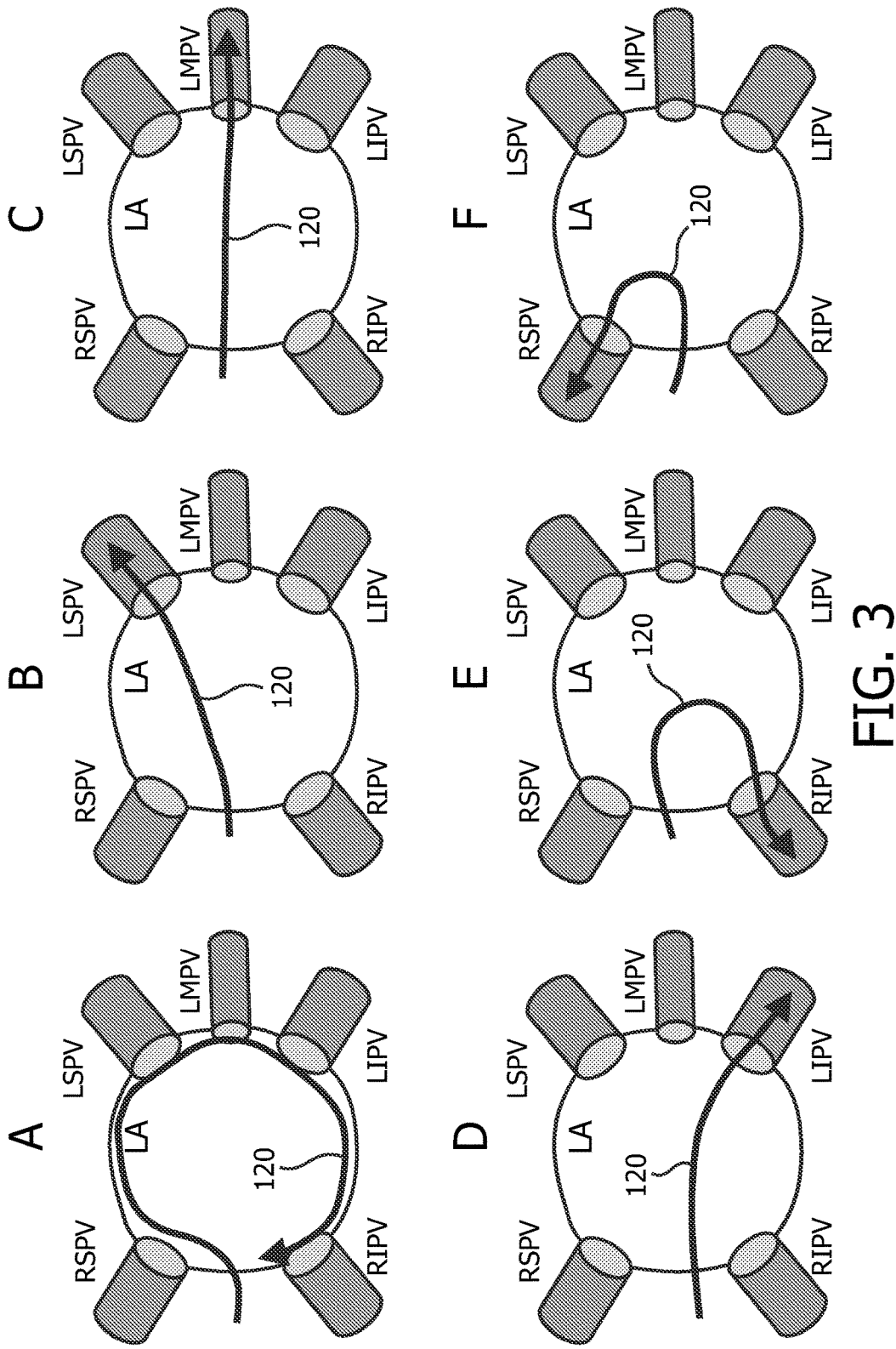
FIG. 3 is a diagram showing a procedure for sweeping portions of a left atrium of a heart to map the left atrium using an optical shape sensing device in accordance with the present principles.

Referring to FIG. 3, an approach for mapping a left atrium (LA) is illustratively shown in accordance with one exemplary embodiment. An optical shape sensing tracked catheter 102 is inserted into the left atrium (LA) and six different configurations (A through F) are performed to map the area. In configuration A, a loop is formed inside the chamber to define the LA lateral boundaries and then is inserted into each individual pulmonary vein (B through F) for definition of chamber shape anchor geometries. The following convention is employed to define the pulmonary veins (PV) in FIG. 3. R=right, L=left, S=superior, I=inferior, and M=medial. The configuration of the optical shape sensing tracked catheter 102 yields data points of a known position to permit mapping of the LA. It should be understood that other anatomical features and acquisition patterns may be employed.

Figure 4:
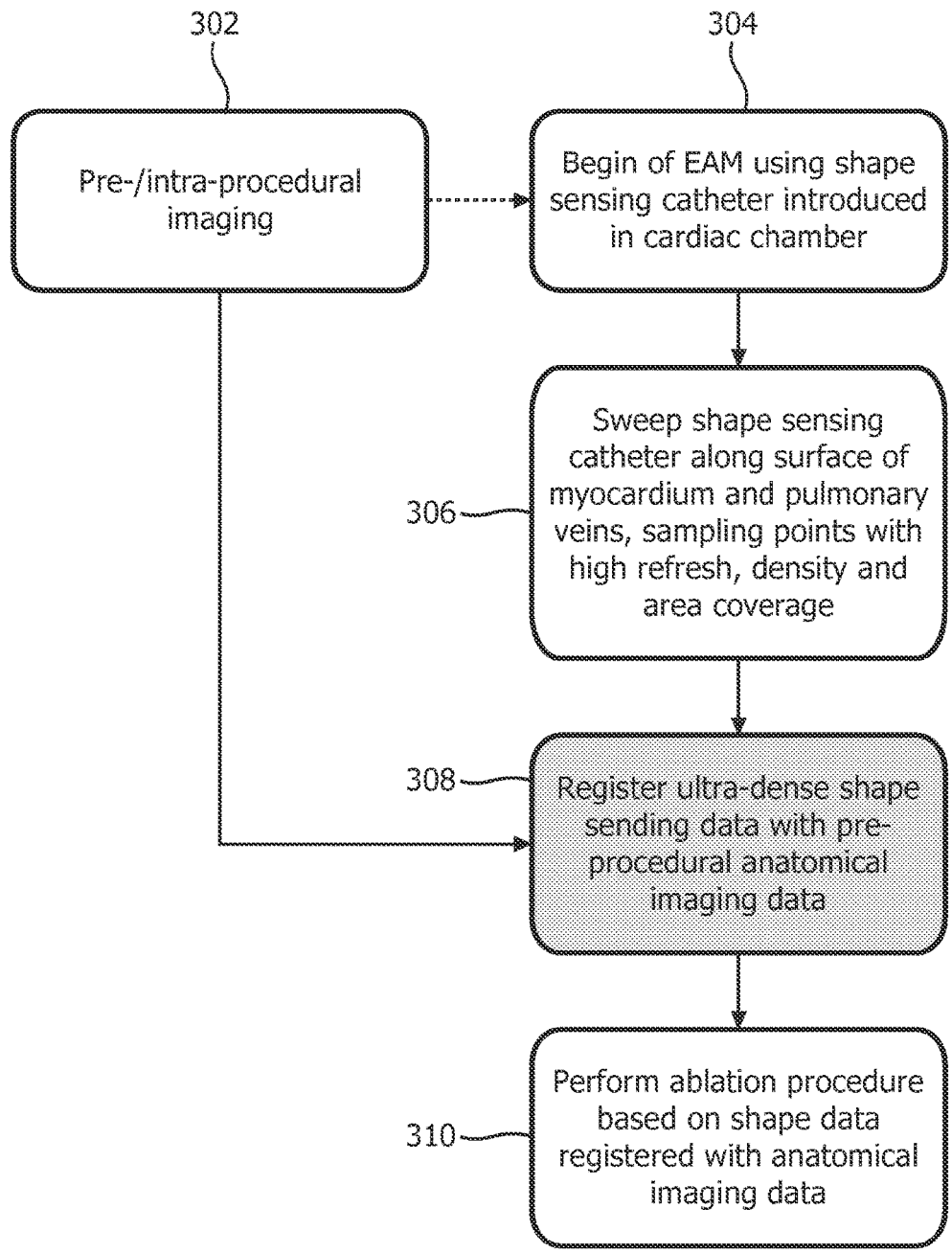
FIG. 4 is a block/flow diagram showing an illustrative system/method for electroanatomic mapping of a portion of the heart in accordance with one embodiment.

Referring to FIG. 4, an illustrative method for mapping a cardiac chamber is described. In block 302, pre-procedural or intra-procedural imaging is employed. This may include X-rays, MRI, CT scan, etc. In block 304, begin EAM using shape sensing catheter or similar instrument introduced to the heart or other structure. In block 306, sweep the shape sensing catheter along a surface of the structure, e.g., the myocardium, pulmonary veins, etc. During the sweep, anatomical points are sampled with a high refresh rate, high density and area of coverage. In block 308, the points sampled with shape sensing catheter are registered with the imaging of block 302. In block 310, an ablation or other procedure can be carried out using the shape data (block 306) registered with the anatomical imaging data (block 302). This provides a more accurate and up-to date rendition of the internal tissues. In particularly useful embodiments, complex ablation procedures in cardiac electrophysiology are performed. Rapid anatomical mapping of vascular or endoluminal spaces for planning of interventional repair procedures (e.g. AAA repair, NOTES procedures) are also enabled.

Figure 5:
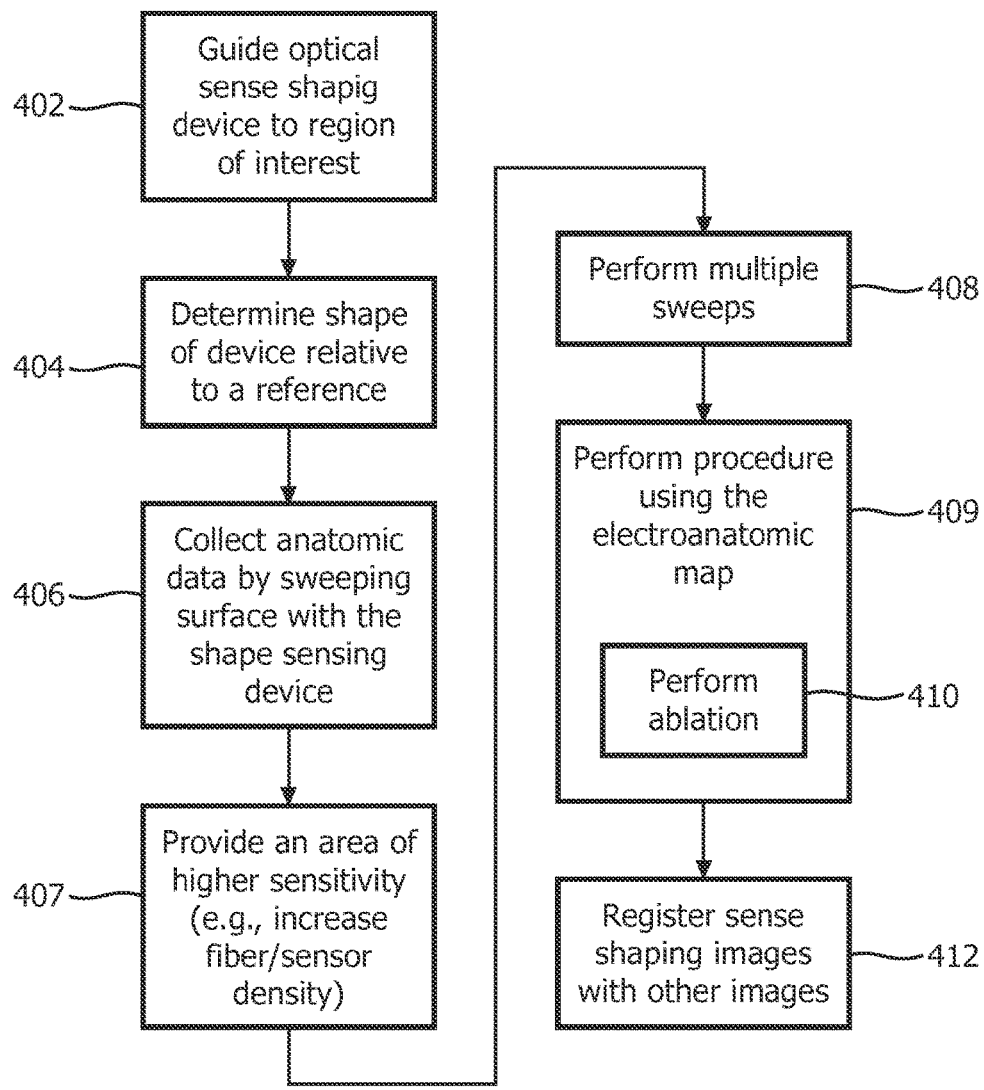
FIG. 5 is a block/flow diagram showing steps for electroanatomic mapping of a region of interest in accordance with an illustrative embodiment.

Referring to FIG. 5, a method for interluminal mapping in accordance with one illustrative embodiment is depicted. In block 402, an elongated flexible instrument having an optical shape sensing device is guided to a region of interest. In block 404, a shape of the flexible instrument is determined relative to a reference. Information about surfaces in the region of interest is collected by sweeping the shape sensing device along a surface to generate an electroanatomic map of the region of interest in block 406. In one embodiment, the electroanatomic map is generated using optical signals from at least one optical fiber having Fiber Bragg Gratings (FBGs) or intrinsic Rayleigh scatter measurement segments for sensing strain in the at least one fiber.

In block 407, an area of higher sensitivity may be provided on a portion of the optical shape sensing device by including an area with a higher number of optical fibers and/or Fiber Bragg Gratings (FBGs) and/or Rayleigh scattering interrogation or the like. In block 408, sweeping the shape sensing device may include contacting the surface with the shape sensing device in different configurations to provide the map. The map may be employed to return to a position in the region of interest.

In block 409, a procedure is performed using at least the electroanatomic map. The elongated flexible instrument may include an imaging enabled ablation device mounted at or near a distal end portion of the flexible instrument and performing a procedure includes ablating tissue in the region of interest in block 410. In block 412, pre or intra-procedural images are registered and/or segmented with or using the map generated using the shape sensing device.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for mapping in medical procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for mapping intraluminal structures, comprising:

an elongated flexible instrument;

an optical shape sensing device that is separate and discrete from the elongated flexible instrument, said optical shape sensing device being disposed within the flexible instrument and configured to determine a shape of an elongated portion of the flexible instrument over an extended length from a distal end of the flexible instrument relative to a reference, the optical shape sensing device configured to collect anatomical information concerning an intraluminal structure based on a configuration of the elongated portion of the flexible instrument during a procedure;

an imaging enabled ablation device mounted at or near the distal end of the flexible instrument; and a shape sensing module configured to receive the information collected by the shape sensing device and generate an electroanatomic volumetric map of a three-dimensional region of the intraluminal structure.

2. The system as recited in claim 1, wherein the optical shape sensing device includes an optical fiber having at least one of Fiber Bragg Gratings (FBGs) and a Rayleigh scatter interrogation setup for sensing strain in the fiber.

3. The system as recited in claim 1, wherein the optical shape sensing device includes an area of higher sensitivity by including an area with a higher number of optical fibers having optical strain sensors.

4. The system as recited in claim 1, wherein the optical shape sensing device includes one of a spiral shape, a ring shape and a loop shape.

5. The system as recited in claim 1, wherein the reference includes one of a position on the flexible instrument and an anatomical reference.

6. The system as recited in claim 1, wherein the flexible instrument includes one of a catheter and an endoscope.

7. The system as recited in claim 1, further comprising an analysis module configured to register a pre or intra-procedural image with the map generated using the shape sensing device.

* * * * *